United States Patent [19] [11] Patent Number: 5,229,288
Mori et al. [45] Date of Patent: Jul. 20, 1993

[54] CYTOTOXICITY TEST METHOD

[75] Inventors: Yuichi Mori, Kanagawa; Toshiaki Takezawa, Isehara; Manabu Yamazaki, Kanagawa, all of Japan

[73] Assignee: W. R. Grace & Co.-Conn., New York, N.Y.

[21] Appl. No.: 690,132

[22] Filed: Apr. 23, 1991

[30] Foreign Application Priority Data

May 2, 1990 [JP] Japan ................................. 2-116687

[51] Int. Cl.$^5$ ...................... C12N 5/00; A61K 31/74; C08J 6/00; C08K 6/00
[52] U.S. Cl. ............................ 435/240.23; 435/240.2; 435/240.21; 523/125
[58] Field of Search ........... 435/240.23, 240.2, 240.21; 424/78, 81; 523/125

[56] References Cited

U.S. PATENT DOCUMENTS 4,963,489 10/1990 Naughton ......................... 435/240.1
5,053,228 10/1991 Mori .................................... 424/486

OTHER PUBLICATIONS

Sutherland, "Cell and Environment Interactions in Tumor Microregions: The Multicell Spheroid Model", *Science*, vol. 240, pp. 177–84, 1988.
Koide et al., "Continued High Albumin Production by Multicellular Spheroids of Adult Rat Hepatocytes Formed in the Presence of Liver–Derived Proteoglycans", *Biochemical and Biophysical Research Communications*, vol. 161, pp. 385–91, 1989.
Enami Laboratory Animal vol. 2 (1) pp. 29–33 1985.
Enami Soshikiki Baiyo Keukyu vol. 4 p. 76 1985.
Sutherland Science vol. 240 pp. 177–84 1988.
Koide et al. Biochemical & Biophysical Research vol. 161 pp. 385–91 1989.

*Primary Examiner*—Michael G. Wityshyn
*Assistant Examiner*—Jane A. Williams
*Attorney, Agent, or Firm*—Vanessa L. Appleby; Jill H. Krafte

[57] ABSTRACT

A cytotoxicity test method is provided which measures the effect of test substances or physical stimulation on cells. The method is both simple and sensitive and is useful for a wide variety of substances and stimulations.

3 Claims, 3 Drawing Sheets

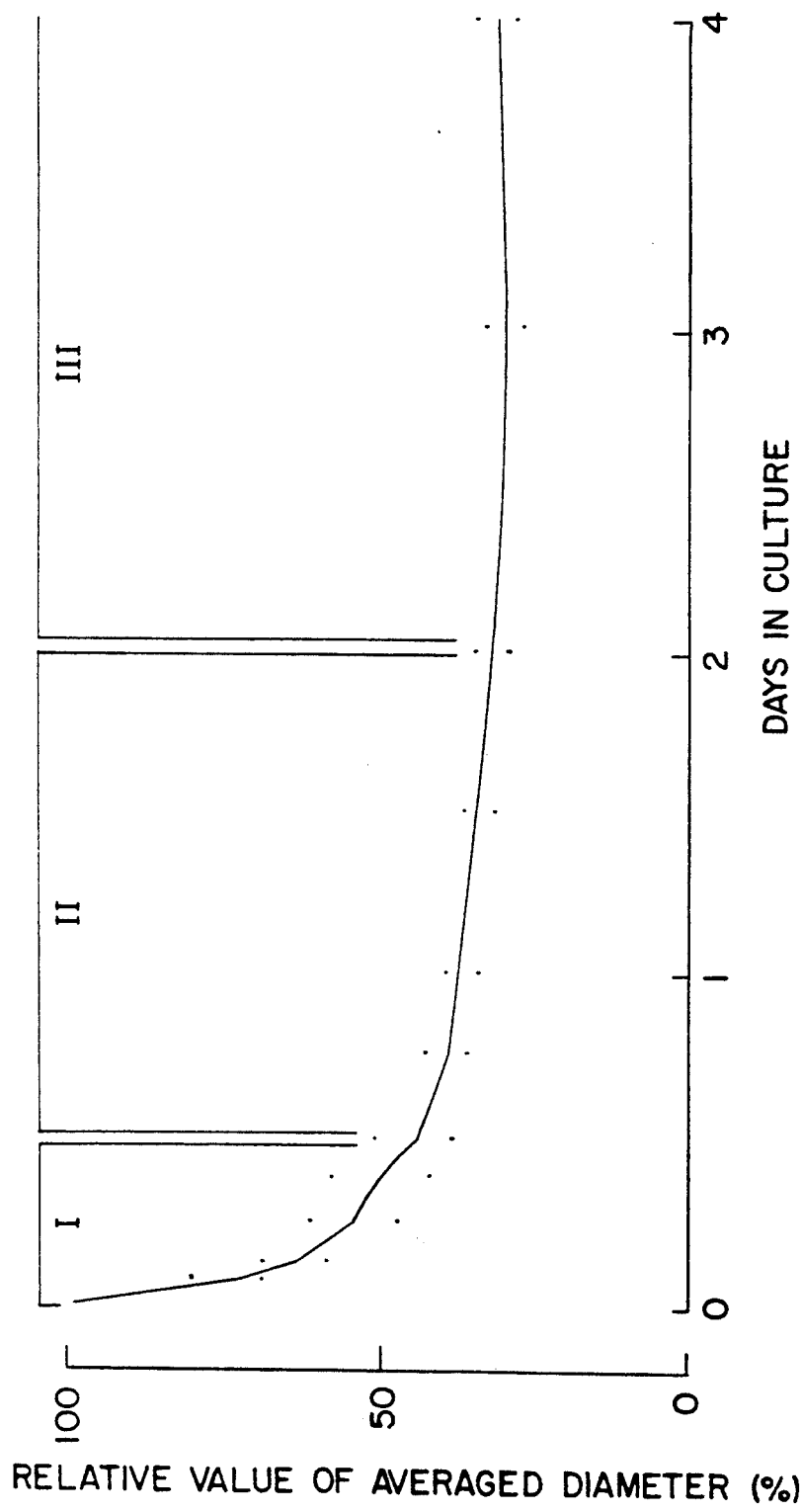

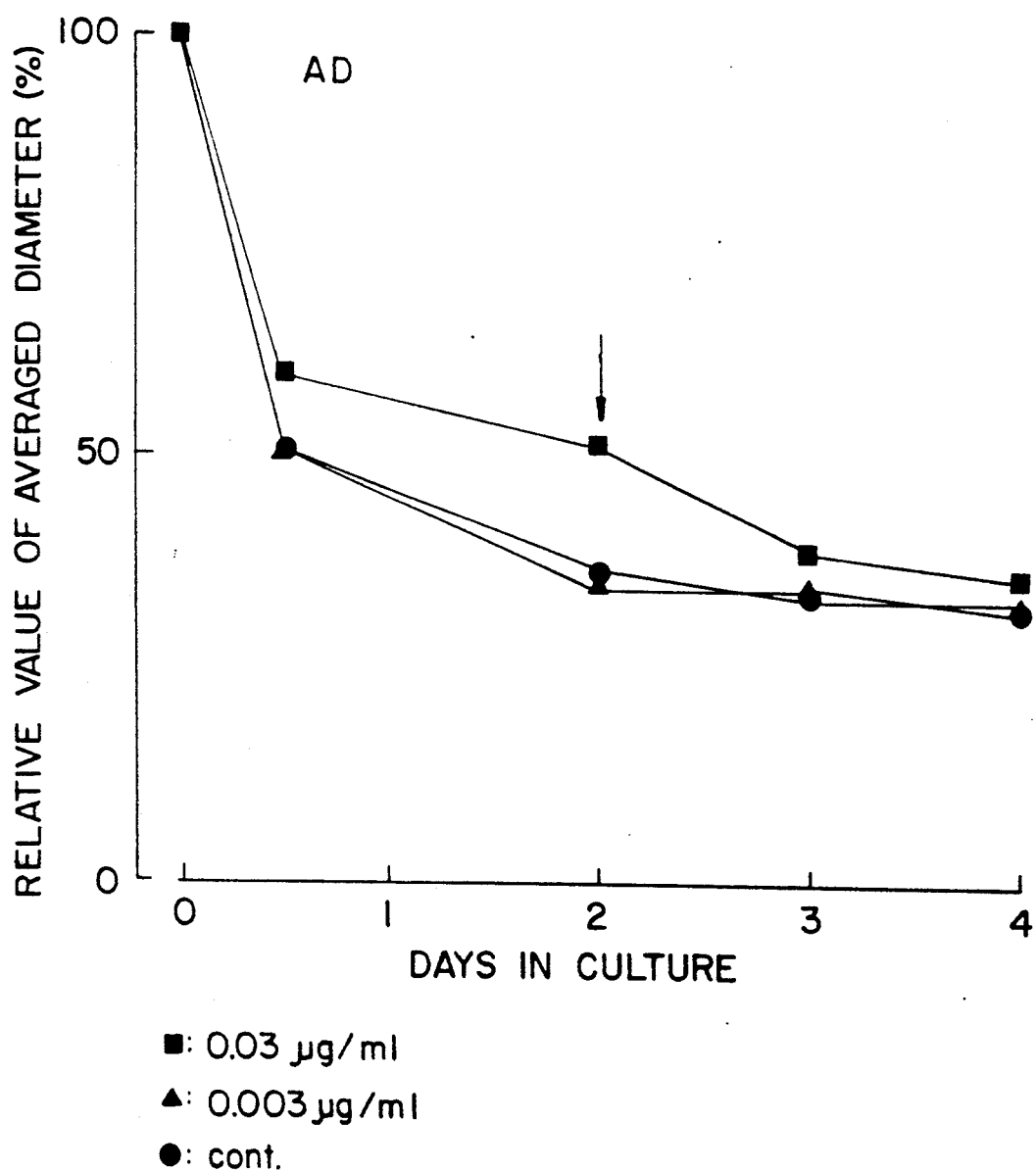

CYTOTOXICITY TEST METHOD

TECHNICAL FIELD

The present invention relates to a cytotoxicity test method which can simply and sensitively measure the effect of various test substances such as drugs, cosmetics, food additives, insecticides or industrial reagents or physical stimulation on cells or aggregated cells. More particularly, the present invention relates to a cytotoxicity test method which can sensitively measure cytotoxicity and the pharmacological activity of test substances and physical activity or stimulation on cell metabolism or intercellular interaction.

BACKGROUND

Cell culture or organ culture systems have been used to evaluate the physiological toxicity or physiological activity of various chemical substances or biologically derived substances. Further, cell culture or organ culture systems have been considered effective for evaluating physiological action or damage of physical stimulations such as temperature, radiation, electrical field or magnetic field to the body.

Organ culture systems have significant advantages over cell culture systems. These advantages include that the relationship between various tissue components and various cells is maintained in a manner similar to that of the body, and therefore organ culture systems are a more meaningful physiological test method. However, organ culture systems have many disadvantages, such as difficulty to supply problems associated with large amounts of living organs, difficulty in duplicating organ function, difficulty in quantifying the effect of the drug due to heterogeneity of the cells or variation of the size of the tissue, difficulty in defining the effect only on the target cells because the system is made of numerous cells, and difficulty associated with culturing the organ systems for a long period of time. Thus, currently organ culture systems are not at a stage which can be used practically as a general cytotoxicity test method.

On the other hand, the following various kinds of culture systems have been practiced as the cytotoxicity test method using cell culture system.

1. Suspension Culture System

The suspension culture system is a culture system where individual cells are separately suspended in culture medium. Animal cells which are used in cell culture systems can be divided into two types, i.e., anchorage independent cells and anchorage dependent cells. Anchorage dependent cells are cells which cannot exhibit normal cells functions such as viability, proliferation and substance-producing ability without the presence of a substrate which serves as the foothold of cells. The majority of normal diploid cells such as the primary cells, and established cell lines which can indefinitely proliferate show anchorage dependency. On the other hand, anchorage independent cells are cells which can exhibit cellular functions such as viability or proliferation without a substrate. Cells of the blood system and cancer cells are anchorage independent. Therefore, suspension culture systems can be applied only to anchorage independent cells, and the majority of the cells forming the tissues or organs are outside the application of the suspension culture system. Since the majority of the target cells used for test substances are anchorage dependent cells, this method has a fatal flaw as a cytotoxicity test method.

2. Monolayer Culture System

The system most commonly used as the culture system of anchorage dependent cells is the monolayer culture system. The monolayer culture system can simply and conveniently test many test substances even if the number of cells is small. Also, the cells can be proliferated and subcultured if necessary. However, the major problem associated with the monolayer culture system is that the majority of organ cells do not exist as a monolayer in the body but rather form a three dimensional structure. Thus, the monolayer culture system is significantly different from the cell structure in the living body. Even with epithelial or endothelial cells, which exist as a monolayer in the living body, the condition under which they are anchored on the artificial substrate used in the monolayer culture system is drastically different from the environment existing in the living body. As illustrated by much experimental evidence, the monolayer culture system is the system which is most suitable for proliferation of cells, since the supply of nutrients and removal of obsolete waste materials can be carried out efficiently in this system. However, monolayer culture is considered unsuitable when it is desirable or necessary for cells to perform a specific function. In other words, monolayer culture is unsuitable as the system to induce differentiation of cells. For testing the physiological effect of test substances on target cells, the monolayer culture system which reduces or loses the specific function of target cells is not suitable as the cytotoxicity test method because it has drastically low sensitivity.

3. Culture System in Gel

As described before, since it is considered that organ cells do not exist in a monolayer state in the living body but rather form a three-dimensional structure, the culture system in gel should be closer to the environment in the living body and more physiological than the monolayer culture system. Numerous experimental data have proven that the specific function of cells or the differentiation induction of cells is more active in gels than in the monolayer culture system [J. Enami: Soshiki Baiyo Kenkyu, 4, 76, 1985]. Today, collagen gel and agar gel, etc. are used in the culture system in gel. But, major flaws of this culture system are the reduced efficiency of the supply of nutrients such as oxygen and the removal of obsolete waste materials, which results in necrosis of cells. Furthermore, with the culture system in gel, the diffusion process of the added test substance to the cells in the interior of the gel is the rate-limiting factor, and thus a quantitative test is difficult.

4. Aggregated Cell Culture System

Aggregated cell culture system is closer to the state existing in the living body and is a better physiological model than the monolayer culture system in the aspect of aggregation of cells that forms a three-dimensional structure.

In many cancer cells, cells are gathered together in suspension culture to form an aggregate [R. M. Sutherland: Science, 240, 177, 1988]. In contrast, it is virtually impossible for normal diploid cells to form an aggregate. However, accidental formation of aggregates of hepatic cells aggregates has been reported on a special culture substrate during monolayer culture [N. Koide, et al.: Biochemical and Biophysical Research Communications, 161, 385, 1989]. However, conventional aggregates, regardless of being a cancer cell or normal cell, were formed accidentally, and thus it was difficult to obtain a large amount of aggregates having a desired size.

Furthermore, like the culture system in gel, the aggregated cell culture system has also a significant problem with the efficiency of the supply of nutrients such as oxygen to the cells and the removal of obsolete waste materials from the cells in the interior of the aggregates. In addition, the diffusion process of the test substance to the cells in the interior of the aggregate becomes a rate-limiting step, and thus a quantitative test is difficult.

Thus, various cell culture systems which are conventionally used as the cytotoxicity test method have been reviewed above. Problems with each system may be summarized below.

(1) Suspension culture system cannot be applied to most of the cells which form tissues and organs.

(2) With monolayer culture system, cells which form various tissues and organs cannot exhibit specific functions. In other words, differentiation of cells is difficult.

(3) With culture system in gel, necrosis of cells occurs due to deficiency in the supply of nutrients to the interior of the gel and to accumulation of obsolete waste materials in the interior of the gel, and diffusion of the test substance to the interior of the gel is a rate-limiting factor.

(4) Aggregated cell culture system can rarely be applied to normal cells, and it is difficult to prepare a large amount of aggregates having a desired size. Moreover, like the culture system in gel, cells in the interior of the aggregates tend to necrotize, and it is difficult to quantify the effect of the drug and so on, because the test substance cannot diffuse into the interior of the aggregates. These are the problems which have to be solved for each culture system.

On the other hand, cell functions such as viability, proliferation ability, and DNA synthesizing ability have been used as the criteria to determine cytotoxicity. The most common method to judge the viability of cells is the dye exclusion test method that employs dyes such as trypan blue, erythromine, or almoin blue and so on. And, a method by which cytotoxicity is judged by release of [$^{51}$Cr or $^{3}$H]-leucine or [$^{3}$H]-proline which has been incorporated in the cells ahead of time from the cell membrane, has been developed also. A typical method is determination of viable cell number and cell morphology. The DNA synthesizing ability is also a good marker to measure the proliferation ability of cells. A method of measuring the incorporation of [$^{3}$H]-thymidine into DNA has been practiced. And, a method of measuring the morphological change of the intracellular organs such as the nucleus or mitochondria as the marker of cytotoxicity has been practiced. In the cytotoxicity test method of this invention, the conventional methods described above can be applied.

Objects

The object of the present invention is to solve various problems of the cytotoxicity test methods which employ the above described conventional cell culture systems.

It is another object of the present invention to provide a cytotoxicity test method which can be applied, not only to the normal cells which form a majority of tissues and organs, but also to cancer cells, and can quantitatively and conveniently measure the effect of a test substance or a physical stimulation on the cells at high sensitivity.

Definition

The term "LCST" is used herein to mean a lower critical solution temperature which is a transition temperature of a temperature-responsive polymeric compound between hydration and dehydration.

SUMMARY OF THE INVENTION

A cytotoxicity test method in accordance with the invention comprises the steps of:

(i) culturing cells on a coating formed on the first cell culture vessel, wherein said coating comprises
 (a) a temperature-responsive polymeric compound having an LCST lower than the cell culture temperature and
 (b) collagen or a mixture of collagen as a major component and at least one adhesive substance as a minor component, at a cell culture temperature higher than said LCST, (ii) maintaining the culture to form a cell sheet on said coating, (iii) lowering the cell culture temperature to a temperature below said LCST to detach said cell sheet from said coating, (iv) transferring said cell sheet to a second cell culture vessel having no adhesiveness for said cell sheet, (v) applying a physical stimulation or adding a test substance to the culture medium for culturing said cell sheet, (vi) culturing said cell sheet in said culture medium, and (vii) measuring the morphological change of said cell sheet in said culture medium.

In another aspect of the invention a cytotoxicity test method comprises, prior to step (iii), the step of applying the same amount of said physical stimulation or adding the same amount of said test substance as in step (v) to the culture medium and further maintaining the culture in the above described cytotoxicity test method.

BRIEF EXPLANATION OF DRAWINGS

FIG. 1 is a graph to illustrate the change of % shrinkage with time in the process of transformation from a cell sheet to a spherical cell aggregate.

FIGS. 2A and 2B are graphs to illustrate the effect of cycloheximide (CH) and actinomycin D (AD) on the change of % shrinkage with time in the process of transformation from a cell sheet to a spherical cell aggregate in comparison with the absence of these substances as shown by "cont."

DETAILED DESCRIPTION OF THE INVENTION

Figure 2A:
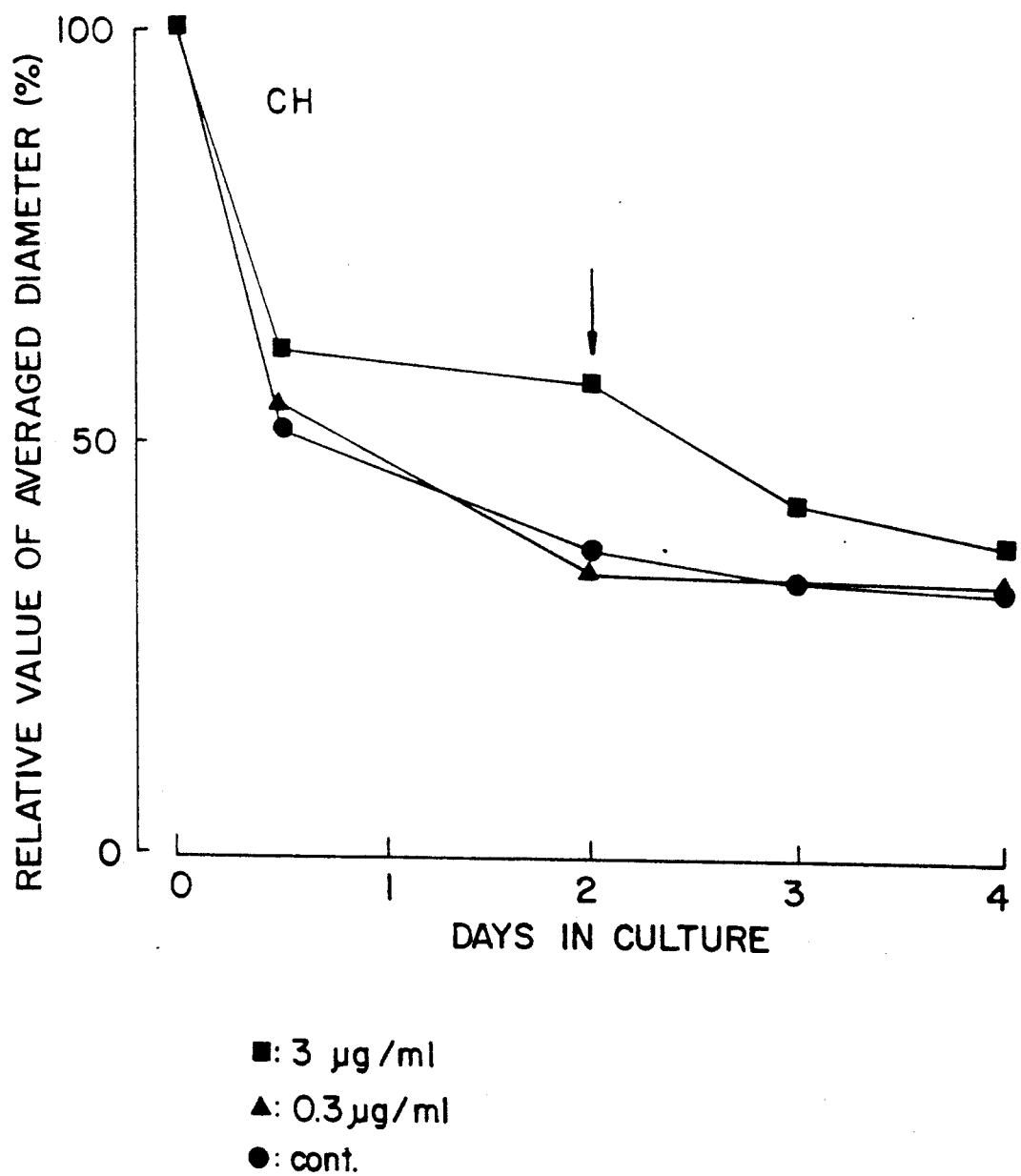

The temperature-responsive polymeric compound having an LCST lower than the cell culture temperature which can be used as one component of the cell culture substrate in the first cell culture vessel of the present invention is in a solid state at the cell culture temperature, and if the temperature is lowered to a temperature below the LCST, the temperature-responsive polymeric compound becomes soluble in the culture medium and the cells on the first cell culture vessel will be detached therefrom.

Examples of the temperature-responsive polymeric compounds having an LCST lower than the cell culture temperature which can be used as one component of the coating on the first cell culture vessel in the present invention are poly-N-substituted (meth)acrylamide derivatives and their copolymers, polymethylvinylether, polyethylene oxide, etherized methylcellulose, and partially acetylated polyvinyl alcohol. Of these preferred compounds more preferred are poly-N-substituted acrylamide derivatives, poly-N- substituted methacrylamide derivatives and their copolymers.

Preferred examples of such temperature-responsive polymeric compounds in the present invention are listed below, but this invention is not limited to these examples. The LCSTs of these polymers rise with the sequence of polymers listed below.

Poly-N-acryloyl piperidine, poly-N-n-propyl methacrylamide, poly-N-isopropyl acrylamide, poly-N,N-diethyl acrylamide, poly-N-isopropyl methacrylamide, poly-N-cyclopropyl acrylamide, poly-N-acryloylpyrrolidine, poly-N,N-ethylmethyl acrylamide, poly-N-cyclopropyl methacrylamide, poly-N-ethyl acrylamide.

The above described polymers may be homopolymers or copolymers with other monomers. Any hydrophilic monomers or hydrophobic monomers can be used as the monomers for copolymerization. Generally speaking, the copolymerization with a hydrophilic monomer will raise the LCST, and the copolymerization with a hydrophobic monomer will lower the LCST. With a proper selection of monomers, a copolymer with a desired LCST can be achieved.

Examples of suitable hydrophilic monomers are N-vinylpyrrolidone, vinylpyridine, acrylamide, methacrylamide, N-methyl acrylamide, hydroxyethyl methacrylate, hydroxyethyl acrylate, hydroxymethyl methacrylate, hydroxymethyl acrylate, acrylic acid, methacrylic acid, vinyl sulfonic acid, and styrylsulfonic acid and their salts, and N,N- dimethylaminoethyl methacrylate, N,N-diethyl-aminoethyl methacrylate, and N,N-dimethylaminopropyl acrylamide and their salts, but the present invention is not limited to these compounds.

Examples of suitable hydrophobic monomers are acrylate derivatives and methacrylate derivatives such as ethyl acrylate, methyl methacrylate and glycidyl methacrylate; N-substituted alkyl (meth)acrylamide derivatives such as N-n-butyl (meth)acrylamide; vinyl chloride, acrylonitrile, styrene and vinyl acetate but the present invention is not limited to these compounds.

The molecular weight of the temperature-responsive polymeric compound which can be employed in the present invention is preferably at least about $1.0 \times 10^5$ and more preferably higher than about $1.0 \times 10^6$. The molecular weight herein means a number average molecular weight obtained from the viscosity. For example, the relationship between the number average molecular weight ($\overline{M}n$) of poly-N-isopropyl acrylamide and its intrinsic viscosity [$\eta$] can be represented by the following equation [S. Ito and R. T. Geronimo, Sen'i Kobunshi Zairyo Kenkyusho Hokoku, No. 159, p. 23 (1988)];

$$[\eta] = 9.59 \times 10^{-5} \overline{M}_n^{0.65}$$

(in tetrahydrofuran solution at 27° C.)

For example, poly-N-isopropylacrylamide (hereinafter referred to as "PNIPAAm") is a polymeric compound which shows a negative temperature coefficient of solubility in water (M. Heskins and J. E. Guillet, J. Macromol. Sci. Chem., A2(8), 1441, 1968). The hydrate (oxonium hydroxide) which depends on the hydrogen bonding formed at a lower temperature between a water molecule and the polymer molecule will decompose at a higher temperature, so that the polymer aggregates by dehydration to form a precipitate. Thus, the transition temperature of this hydration and dehydration is called "lower critical solution temperature" or "LCST". Thus, at a temperature above the LCST, the polymer aggregates to form a solid state, but at a temperature lower than the LCST, the polymer dissolves in water.

The present invention takes advantage of such properties of the temperature-responsive polymeric compounds.

Any type of collagen can be used as the other component of the cell culture substrate of the first cell culture vessel in the present invention. The adhesive substances which can be used as a minor component together with collagen as a major component include fibronectin, laminin, vitronectin, proteoglycan, glycosaminoglycan, thrombospondin, gelatin, lectins, anchorage oligopeptides and adhesive proteins isolated from shellfish.

The mixing weight ratio of the temperature-responsive polymeric compound to collagen or a mixture of collagen as a major component and the adhesive substance is typically from about 1:1 to about 1:3.

The coating on the first cell culture vessel consists of the temperature-responsive polymeric compound having an LCST lower than the cell culture temperature and collagen or a mixture of collagen and the adhesive substance. Such a coating is formed on the first cell culture vessel by coating an aqueous solution of the mixture of the temperature-responsive polymeric compound and collagen or a mixture of the collagen and the adhesive substance on the first cell culture vessel at a temperature below the LCST and drying the coating thus obtained. The coating is also prepared by dipping the first cell culture vessel into the aqueous mixture solution of the temperature-responsive polymeric compound and collagen or a mixture of collagen and the adhesive substance at a temperature below the LCST and drying the coating thus obtained.

The thickness of the coating after it is dried is at least about 0.2 μm, preferably at least 0.5 μm and more preferably at least about 1.0 μm. When the thickness is below about 0.2 μm, the cell detachability remarkably worsens and it takes a very long time for the detachment of the cells and as a result, the cell functions are rendered unstable.

According to the cytotoxicity test method of the present invention, cells are cultured on a coating of the cell culture substrate formed on the first cell culture vessel of a monolayer system suitable for the proliferation of anchorage dependent cells at a cell culture temperature higher than the LCST of the temperature-responsive polymeric compound. When the cell culture substrate is fully covered with the cells, the cell culture temperature is lowered to a temperature below the LCST. As a result, the cultured cells can be detached from the cell culture substrate in the form of a cell sheet or monolayer which maintains the intercellular junctions without causing any damage to the cells.

Then, the detached cell sheet is transferred onto a non-adhesive substrate of the second cell culture vessel where a physical stimulation is applied or a test substance is added to the culture medium for the cell sheet, and the cell sheet is further cultured. The cell sheet, by suspension culture, changes into a three dimensional cell aggregate. Since the morphological change of such a cell aggregate depends on the applied physical stimulation or the added test substance, the degree of cytotoxicity can be evaluated by measuring the morphological change of the cell aggregate.

In the present invention the physical stimulation or the test substance can be applied or added to the culture medium, and the culture can be maintained prior to the lowering of the cell culture temperature to a temperature below the LCST in the first cell culture vessel. The term "morphological changes" used herein includes not only the external change such as size and form of the cells but also any detectable changes such as change of intracellular organs and intercellular linkages and so on.

The "physical stimulation" to be applied to the culture system broadly includes temperature, radiation, electrical field, magnetic field, light, microwave, and so on. The "test substance" to be added to the culture system broadly includes chemical substances such as medicinal drugs, cosmetics, food additives, insecticides and industrial reagents and so on. And, the setting or the change of the culture conditions such as oxygen concentration, pH and nutritional condition are also included in the meaning of the term "application of a physical stimulation or addition of a test substance.

As described above, many normal cells which form tissues and organs and the established cells which can indefinitely multiply are anchorage dependent cells, and therefore the monolayer culture system is absolutely necessary for the multiplication of the cells. Therefore, the first step in this invention plays a role of increasing the number of cells to a quantity necessary for the cytotoxicity test by culturing the cells in monolayer. However, in the monolayer culture system, the cells anchored and multiplied on the substrate are significantly different from the cell state in a actual living body, and thus they are unsuitable as the system for each individual cell to show its characteristic function and as a system to induce differential function of the cells. Thus, the characteristic function to serve as the target cells in the test of test substances or test of physical effect is decreased or lost, and thus the sensitivity of the cytotoxicity test method will decline drastically.

The second step of this invention is a process to activate the characteristic function of the cells, which have declined in the monolayer culture system. Thus, the cells are detached from the substrate which has restricted the cells function in the monolayer state which is different from the living environment. Then the cells are transferred from the monolayer state to the three dimensional culture system which is closer to the environment existing within the living body, to induce the differential function of the cells and to improve the sensitivity of the cytotoxicity method.

On the other hand, as mentioned before, the problems with the conventional three-dimensional culture method such as the culture method in gel and aggregated cell culture method, include (1) test substances cannot reach the interior of the three-dimensional culture system and it is difficult to quantitatively evaluate the drug effect, and (2) cells may necrotize because supply of nutrients or removal of waste materials cannot be carried out efficiently in the interior of the culture system. These problems can be solved by using the culture system of this invention. Problem (1) can be solved in the first step of this invention by addition of a test substance in the monolayer system which allows the test substance to reach homogeneously all cells. On the other hand, problem (2) is drastically reduced since in the second step of this invention the cell sheet is detached from the substrate and a three-dimensional structure is gradually formed. The risk of necrosis of internal cells will be drastically reduced, compared to the conventional culture system in gel or aggregated cell culture system which forms a tight structure from the start. Furthermore, since the test method of this invention is carried out mainly in the transition state until a three-dimensional structure is formed from the cell sheet and the test is completed by the time when a perfect three-dimensional structure is formed, the risk of necrosis is further reduced.

Another characteristic feature of the culture system to be used in the cytotoxicity test of this invention is that it does not use trypsin/EDTA which is the cell detaching agent conventionally used to detach cultured cells from the surface of a substrate. Cell detaching agents such as trypsin/EDTA, not only destroy the bond between cells and the substrate, but also destroy the tight junction, desmosome, or gap junction which is the intercellular bonds, and thus it separates the cells into individual cells. Therefore, it is impossible to form a cell sheet or a cell aggregate. Furthermore, these cell detaching agents destroy various membrane receptors which exist on the surface of the cell membrane, and cause significant damage to the susceptibility of cells to signaling molecules such as hormone and local chemical mediators. Therefore, detachment of cells by conventional detaching agents will significantly reduce the sensitivity of the cytotoxicity test.

As described before, conventional methods of measuring cellular functions such as cell viability, proliferation ability, and DNA synthesizing ability, can naturally be applied in the cytotoxicity test method of the present invention. However, these methods are indirect in the aspect of damage to the aggregates of cells because these cellular functions are markers of toxicity mainly against individual cells. In a living body, cells do not exist individually, but instead they form a society by the strong intercellular interaction and function as a member of that society. The cytotoxicity test method of the present invention is suitable for the determination of toxicity against cell aggregates (cell society) rather than against individual cells and therefore, the evaluation of the conditions closer to the cytotoxicity occurring actually in the body is possible. Particularly, the method of the present invention can measure the effect of test substances on the morphological change of the entire cell aggregates as it shifts from the cell sheet to the cell aggregate, the effect on the morphological change of the intracellular organs and intercellular junctions within the cell aggregates, and the effect on the distribution of stained cells in the aggregates by the stain method and so on, and thus many toxicity models of tissues and organs can be provided.

Examples are illustrated below to further explain this invention, but the scope of this invention is not intended to be limited by such examples.

Control Example

N-Isopropylacrylamide monomer (here "NIPAAm", a product of Eastman Kodak Co.) 50 g was dissolved in 500 ml benzene. 2,2′-Azobisisobutyronitrile (here "AIBN") 0.2 g was used as the polymerization initiator. Polymerization was carried out at 60° C. for 12 hours in a stream of nitrogen gas with constant agitation. The polymer thus obtained was precipitated in benzene and after decantation the precipitates formed were dissolved in tetrahydrofuran and purified with ethyl ether. The poly-N-isopropyl acrylamide (here "PNIPAAm") thus prepared had a number average molecular weight of $2.0 \times 10^6$ and the LCSTs of the PNIPAAm in PBS and culture medium [polymer concentration: 1% (w/v)] were 28.9° C.± 0.1° C. and 28.6° C.±0.1° C. Using the PNIPAAm as obtained above, an aqueous 0.5% (w/v) solution was prepared, and the solution was sterilized by filtering through a 0.45 μm filter. The aqueous polymer solution thus obtained was mixed with an equal amount of the aqueous 0.5% (w/v) solution of type I collagen which was solubilized from a cow's skin by pepsinization (sterilized, a product of Kohken K. K.), to prepare a mixed solution of the PNIPAAm and the collagen. This mixed solution was poured on the bottom of a commercially available plastic culture dish (Falcon, 35 mm), and it was air-dried aseptically in a clean bench at about 10° C. A dish where a 1:1 mixture of collagen and PNIPAAm was coated on the bottom of the dish to a thickness of about 2.0 μm was prepared by the above described method. Fibroblasts derived from human skin were suspended in Dulbecco's modified Eagle medium ("DMEM", a product of GIBCO, containing 10% (w/v) calf serum) (cell concentration in the suspension: about $2 \times 10^5$ cells/ml). Two milliliters of this cell suspension was incubated at 37° C., and then it was poured in the coated dish which was pre-incubated at 37° C. It was cultured at 37° C. for 3 days in an air/5 volume% $CO_2$ gas incubator. After 3 days at which point the cultured cells covered the surface of the bottom of the dish completely, the dish was taken out from the 37° C. incubator and left to stand at 4° C. on ice. After the cell sheet was completely detached from the surface of the bottom of the dish, the old medium was discarded and the sheet was washed twice with fresh medium at 4° C. to remove the dissolved polymer and the collagen. Then, the cell sheet was transferred and incubated in a hydrophobic dish (Falcon, 35 mm containing 2 ml of fresh medium. In this culture system the cell sheet gradually shrank and finally became a spherical cell aggregate having an outer diameter of about 900 μm.

During the shrinking process, the cell aggregate was examined at different times by a phase contrast microscope. Size (average values of longer diameter and shorter diameter) of the cell aggregate was measured, and % shrinkage which is a relative value considering the diameter of the cell sheet immediately after the detachment as 100% was calculated, and the results were plotted against time as shown in FIG. 1. As clearly shown in FIG. 1, the shrinkage process can be divided into three phases. Thus, phase I is a very significant shrinkage period for about 0.5 day from the time of the detachment of the cell sheet, phase II is a weak shrinkage period for about 2 days after the 0.5 th day and phase III is a stabilized period without shrinkage after the second day.

EXAMPLE 1

The fibroblasts derived from human skin were cultured for 3 days on a dish coated with the mixture of PNIPAAm and collagen as described in Control Example in the same manner as in Control Example. After a cell sheet was detached and transferred onto a hydrophobic dish in the same manner as in the Control Example, cycloheximide (here "CH") was added to the culture medium for the cell sheet to bring the concentration to 0.3 and 3μg/ml of medium, respectively. The shrinkage process of the detached cell sheet was examined by the phase contrast microscopy while the cell sheet was cultured in the culture medium containing CH in the hydrophobic dish. The shrinkage behavior of the cell aggregate is shown in FIG. 2A. As shown in FIG. 2A the shrinkage behavior of phase II ranging from the 0.5 th to the second day after the detachment was completely interrupted by the addition of more than 3 μg/ml of CH and no formation of any spherical cell aggregate was observed. At the second day after detachment, as shown in FIG. 2A by an arrow sign, the added CH was completely removed by washing the cell aggregate with fresh culture medium and then transferring it into the vessel containing fresh culture medium. As shown in FIG. 2A immediately after the removal of CH, the shrinkage started again. Since CH is an inhibitor of protein synthesizis, the shrinkage process of phase II seems to be closely related to the protein synthetic process by the cell.

EXAMPLE 2

The fibroblasts derived from human skin were cultured for 3 days on the dish coated with the mixture of PNIPAAm and collagen as used in Control Example in the same manner as Control Example. Twelve hours before a cell sheet was detached from the cell culture substrate and transferred onto a hydrophobic dish in the same manner as in Control Example, actinomycin D (here "AD") was added to the culture medium to bring the concentration to 0.003 and 0.03 μg/ml of medium, respectively. Then the shrinkage process of the detached cell sheet was examined by phase contrast microscopy while the detached cell sheet was cultured in the culture medium containing 0.003 and 0.03 μg/ml (medium) of AD, respectively, in the hydrophobic dish. The shrinkage behavior of the cell aggregate is shown in FIG. 2B. As shown in FIG. 2B, the shrinkage behavior of phase II ranging from the 0.5 th to the second day after the detachment was significantly interrupted by the addition of more than 0.03 μg/ml of AD and no formation of any spherical cell aggregate was observed. At the second day after the detachment as shown in FIG. 2B by an arrow, the added AD was completely removed by washing the cell aggregate with fresh culture medium and then transferring it into the vessel containing fresh culture medium. As shown in FIG. 2B, immediately after the removal of AD, the shrinkage started again. The concentration of AD which inhibits phase II was about 1/100 of that of CH. Since AD is an inhibitor of the mRNA synthesis, the shrinkage process of the phase II seems to be closely related to the mRNA synthesis of the cell.

Comparative Example

The fibroblasts derived from human skin as used in Example 1 were cultured for 3 days on a plastic tissue culture dish (Falcon, 35 mm), and then cycloheximide and actinomycin D were added, respectively, in such an amount that the concentration of the medium would be 10 μg/ml, and the morphological change of the cells was examined under a phase contrast microscope. No morphological change was observed at all. As shown in Example 1, illustrating the cytotoxicity test method of this invention, cytotoxicity was noted with cycloheximide at 3 μg/ml and with actinomycin D at 0.03 μg/ml. In contrast, the concentration for the detection of cytotoxicity by the conventional monolayer culture such as shown in this Comparative Example was higher than 10 μg/ml. Thus, the sensitivity was significantly lower, compared to the culture system of this invention.

As stated above, the cytotoxicity test method using the cell culture system of the present invention is more convenient and has better sensitivity than the conventional method. Furthermore, the cell culture system of the present invention can measure sensitively the intercellular interaction or the effect on the cell aggregates, which has been difficult to evaluate by the methods of the prior art.

We claim:

1. A method for evaluating cytotoxicity which comprises the steps of:
   (i) culturing cells on a coating formed on a first cell culture vessel, wherein said coating comprises
      (a) a temperature-responsive polymeric compound having an LCST lower than the cell culture temperature and
      (b) collagen or a mixture of collagen as a major component and at least one adhesive substance as a minor component, at a cell culture temperature higher than said LCST,
   (ii) maintaining the culture to form a cell sheet on said coating,
   (iii) lowering the cell culture temperature to a temperature below said LCST to detach said cell sheet from said coating,
   (iv) transferring said cell sheet to a second cell culture vessel having no adhesiveness for said cell sheet,
   (v) applying a physical stimulation or adding a test substance to the culture for culturing said cell sheet,
   (vi) culturing said cell sheet in said culture to form a steroid, and
   (vii) comparing the morphological change in the transformation process from said cell sheet to said spheroid in said culture in the presence of said physical stimulation or said test substance with the morphological change in the absence of said physical stimulation or said test substance.

2. The method of claim 1 comprising, prior to step (iii), the step of applying the same amount of said physical stimulation or adding the same amount of said test substance as in step (v) to the culture and further maintaining the culture.

3. The method of claim 1, wherein said temperature-responsive polymeric compound is selected from the group consisting of a poly-N-substituted acrylamide derivative or copolymer thereof, a poly-N-substituted methacrylamide derivative or copolymer thereof, polyvinylmethylether, and a partially acetylated polyvinylalcohol.

* * * * *

UNITED STATES PATENT AND TRADEMARK OFFICE
CERTIFICATE OF CORRECTION

PATENT NO. : 5,229,288

DATED : July 20, 1993

INVENTOR(S) : Y. Mori, T. Takezawa, M. Yamazaki

It is certified that error appears in the above-identified patent and that said Letters Patent is hereby corrected as shown below:

IN THE CLAIMS:

Claim 1, Column 12, line 10, delete "steroid", and insert -- spheroid -- therefor.

Signed and Sealed this

Nineteenth Day of July, 1994

Attest:

BRUCE LEHMAN

Attesting Officer    Commissioner of Patents and Trademarks